United States Patent [19]
Fried

[11] Patent Number: 5,239,116
[45] Date of Patent: Aug. 24, 1993

[54] PREPARATION OF SECONDARY ALKOXYALKANOIC ACIDS

[75] Inventor: Herbert E. Fried, Houston, Tex.

[73] Assignee: Shell Oil Company, Houston, Tex.

[21] Appl. No.: 969,657

[22] Filed: Oct. 30, 1992

[51] Int. Cl.$^5$ .................... C07C 51/16; C07C 51/235; C07C 51/245; C07C 51/27
[52] U.S. Cl. ................................ 562/537; 562/538; 562/540; 562/587
[58] Field of Search ............... 562/540, 537, 538, 587; 568/402, 471

[56] References Cited

U.S. PATENT DOCUMENTS

| | | | |
|---|---|---|---|
| 4,620,033 | 10/1986 | Isshiki et al. | 562/519 |
| 5,136,101 | 8/1992 | Fried. | |
| 5,136,102 | 8/1992 | Fried. | |
| 5,136,103 | 8/1992 | Fried. | |
| 5,155,278 | 10/1992 | Fried. | |
| 5,155,279 | 10/1992 | Fried. | |
| 5,175,359 | 12/1992 | Fried | 562/540 X |

FOREIGN PATENT DOCUMENTS 50-96516 7/1975 Japan.

OTHER PUBLICATIONS

Miyazawa et al., "Oxidation of Benzyl Alcohol with Iron (III) Using Polymers Containing Nitroxyl Radical Structure as a Mediator," J. Polym. Sci., Polym. Chem. Ed., 23 (9), 1985, pp. 2487-2494.

Grigor'ev et al., "Participation of Nitroxyl Radical in the Oxidation of Aldehyde and Alcohol Groups in 3-imidazolin-1-oxyls," Izc. Akad. Nauk SSSR, Ser. Khim, (1), 1978, pp. 208-210.

Miyazawa et al., "Oxidation of Benzyl Alcohol with Copper(II) Mediated by a Polymeric Oxoaminium Salt," J. Mol. Catal., 49(1), 1988, 131-134.

Ganem et al., "Biological Spin Labels as Organic Reagents. Oxidation of Alcohols to Carbonyl Compounds Using Nitroxyls," J. Org. Chem., 40(13), 1975, pp. 1998-2000.

Miyazawa et al., "Oxidation of Benzyl Alcohol by Iron-(III) Mediated by Nitroxyl Radical," J. Mol. Catal., 31(2), 1985, pp. 217-220.

Anelli et al., "Fast and Selective Oxidation of Primary Alcohols to Aldehydes or to Carboxylic Acids and of Secondary Alcohols to Ketones Mediated by Oxoammonium Salts under Two-Phase Conditions," J. Org. Chem., 52 (12), pp. 2559-2562, Aug. 1986.

Inokuchi et al., "A Selective and Efficient Method for Alcohol Oxidations Mediated by N-Oxoammonium Salts in Combination with Sodium Bromite," J. Org. Chem., 1990, 55, pp. 462-466.

Organic Synthesis, vol. 69, p. 212 (1990).

Semmelhack et al., "Oxidation of Alcohols to Aldehydes with Oxygen and Cupric Ion, Mediated by Nitrosonium Ion," J. Am. Chem. Soc. 1984, 106, 3374-3376.

Yamaguchi et al., "Application of Redox System Based on Nitroxides to Organic Synthesis," Pure & Applied Chemistry, vol. 62(2), 1990, 217-222.

*Primary Examiner*—Arthur C. Prescott
*Attorney, Agent, or Firm*—Pamela J. McCollough

[57] ABSTRACT

A process for the preparation of a secondary alkoxyalkanoic acid by reacting the corresponding secondary alkoxyalkanol with a stable free radical nitroxide in the presence of a $NO_x$-generating compound and an oxidant at a temperature in the range of from about 0° C. to about 100° C. and thereafter separating out the secondary alkoxyalkanoic acid.

20 Claims, No Drawings

PREPARATION OF SECONDARY ALKOXYALKANOIC ACIDS

FIELD OF THE INVENTION

This invention relates to a process for the preparation of secondary alkoxyalkanoic acids by the oxidation of the corresponding secondary alkoxyalkanols in the presence of a stable free radical nitroxide, a $NO_x$-generating compound and an oxidant.

BACKGROUND OF THE INVENTION

Secondary alkoxyalkanoic acids are useful as anionic detergents. These acids, being composed of only the elements C, H and O, do not pose the environmental problems that other detergents containing heteroatoms such as N, S, and P pose. The alkoxyalkanoic acids can be prepared in a three-step process by first reacting a secondary alkanol with ethylene oxide and an acid catalyst, then reacting the resultant seed alkoxylate with an alkaline catalyst and ethylene oxide and thereafter converting the secondary alkoxyalkanol to an alkoxyalkanoic acid.

Japanese Patent No. 50-96516, issued Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C. -270° C. These high temperatures can degrade the ether linkages especially in the highly ethoxylated alcohols.

It is known to use nitroxyl radicals/oxoammonium salts in the oxidation of primary alcohols to produce aldehydes and acids and secondary alcohols to ketones. *Journal of Organic Chemistry*, vol. 52 (12), pp. 2559-2562; *Pure and Applied Chemistry*, vol. 62(2), 1990, pp. 217-222; *Journal of Organic Chemistry*, vol. 55, 1990, pp. 462-466. The primary products produced in these processes are aldehydes and the stoichiometrically consumed oxidant is hypochlorite.

It is generally more difficult to oxidize secondary alkoxyalkanols than alkanols or primary alkoxyalkanols as it is difficult to oxidize secondary alkoxyalkanols without splitting the molecular chain at the ether linkage at the secondary carbon and thereby producing a large proportion of undesired by-products. Secondary alkoxyalkanols are much prone to this cleavage reaction relative to primary alkoxyalkanols due to the greater lability of the secondary versus primary ether linkage.

It is therefore an object of this invention to produce secondary alkoxyalkanoic acids in high yields and with high selectivities from secondary alkoxyalkanols without producing large amounts of other products such as olefins and polyethylene glycols.

It is a further object of this invention to provide a process for the preparation of secondary alkoxyalkanoic acids in which highly corrosive, difficult to separate, side-products are not formed.

It has been found that secondary alkoxyalkanoic acids can be produced in high yields and with high selectivities by using catalytic amounts of a stable free radical nitroxide, a $NO_x$-generating compound and an oxidant.

SUMMARY OF THE INVENTION

This invention relates to a process for the preparation of a secondary alkoxyalkanoic acid of the formula:

wherein R is a secondary alkyl group having from 3 to about 1000 carbon atoms, R' is hydrogen or alkyl or mixtures thereof (on the individual molecule) and n is an integer of from 1 to about 200 which comprises reacting the corresponding secondary alkoxyalkanol with a stable free radical nitroxide having the formula:

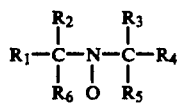

wherein
(1) (a) each of $R_1$, $R_2$, $R_3$ and $R_4$ is an alkyl, aryl or heteroatom substituted alkyl group having 1 to about 15 carbon aotms, and (b) $R_5$ and $R_6$ (i) each is an alkyl group having 1 to about 15 carbon atoms provided that $R_1$-$R_6$, are not all alkyl groups, or a substituted alkyl group having 1 to about 15 carbon atoms wherein the substituent is hydrogen, cyano, —$CONH_2$, —$OCOCH$, $OCOC_2H_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of O or N, or
(2) the

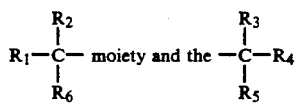

moiety individually are aryl, in the presence of a $NO_x$-generating compound and an oxidant at a temperature in the range of from about 0° C. to about 100° C. and thereafter separating out the secondary alkoxyalkanoic acid.

DESCRIPTION OF THE PREFERRED EMBODIMENTS

The present process converts secondary alkoxyalkanols of the formula $$RO(CH_2CHR'O)_nCH_2CH_2OH \quad \text{(I)}$$

wherein R is a secondary alkyl group having preferably 3 to about 1000; more preferably about 3 to about 45 carbon atoms, and most preferably from about 8 to about 18 carbon atoms, R' is hydrogen or alkyl, preferably methyl, or mixtures thereof (on the individual molecule) and n represents the average number of oxyalkylene groups and is an integer of from 1 to about 200, preferably of from about 1 to about 9, to the corresponding secondary alkoxyalkanoic acids of the formula:

$$RO(CH_2CHR'O)_nCH_2CO_2H \quad \text{(II)}$$

by contacting the secondary alkoxyalkanol with a stable free radical nitroxide in the presence of a $NO_x$-generating compound and an oxidant at a temperature in the range of from about 0° C. to about 100° C. and thereafter separating out the secondary alkoxyalkanoic acid.

The R group in the above formula I can be substituted with any substituent which does not interfere with the oxidation of the hydroxy group. Such substituents include —OR", —CH$_3$, —COOH, CONH$_2$ and COOR" wherein R" is an alkyl or aryl group.

The secondary alkoxyalkanol reactant suitably comprises one or more secondary alkanols having a carbon number in the range of from about 3 to about 1000, preferably from about 3 to about 45, more preferably from about 6 to about 30, and most preferably from about 8 to about 18, to which from about 1 to about 200 moles, preferably from about 1 mole to about 50 moles, and more preferably from about 1 mole to about 9 moles, of alkylene oxide per mole of secondary alcohol has been added. The secondary alkoxyalkanols are typically prepared by the reaction of a secondary alkanol with between about 1 and about 4 moles of alkylene oxide per mole of secondary alkanol in the presence of an acidic (e.g., Lewis acid) catalyst to prepare a seed alkoxylate mixture, and the reaction of the seed alkoxylate mixture in the presence of an alkaline catalyst with sufficient additional alkylene oxide to produce a secondary alkanol alkoxylate mixture characterized by an average of between about 3 and about 15 alkylene oxide adducts in the ether substituents of the alkoxylate molecules.

Secondary alkanols suitable for use in preparing the secondary alkoxyalkanol reactant include C$_3$ to C$_{1000}$, preferably C$_3$ to C$_{45}$ secondary mono-alkanols. As a general rule, the carbon chains of the secondary alkanols may be of either branched or linear (straight-chain) structure, although preference exists for secondary alkanols in which greater than about 50 percent, more preferably greater than about 70 percent and most preferably greater than about 90 percent of the molecules are of linear (straight-chain) carbon structure. Specific secondary alkanols and commercially available secondary alkanols and secondary alkanol mixtures are well known and are suitable. Commercially available mixtures of secondary alkanols prepared via the oxidation of paraffins, and from internal olefins and alpha-olefin mixtures via sulfation and hydrolysis reactions are particularly suitable for use in preparing the secondary alkoxyalkanol reactant in the present invention.

Suitable examples of secondary alkoxyalkanols for use in the present invention which are commercially available include Tergitol 15-S-7 and Tergitol 15-S-9, both trademarks of and sold by Union Carbide ethoxylates. Tergitol 15-S-7 is a mixed ethoxylate product of 11 to 15 carbon atoms of linear secondary alkanol with 7 moles of ethylene oxide and Tergitol 15-S-9 is a mixed ethoxylate product of 11 to 15 carbon atoms of linear secondary alkanol with 9 moles of ethylene oxide.

The process of the instant invention is particularly suited to detergent range ethoxylated, propoxylated or alkoxylated alcohols with secondary alkyl chains of about 8 to about 20, preferably of about 11 to about 18 carbon atoms. In the case of propoxylated or alkoxylated secondary alkanols, it is necessary to further ethoxylate in order to obtain alkoxyalkanoic acids. The R' groups on an individual molecule can be hydrogen, methyl or mixtures thereof. For example, straight ethoxylated, straight propoxylated and mixed ethoxylated-propoxylated detergent range secondary alcohols are commercially available. The number of such alkoxylate groups, (CH$_2$CHR'O), ranges from 1 to about 20. In a preferred embodiment, the starting secondary alkoxyalkanol is an ethoxylated secondary alcohol which has had the unreacted secondary alcohols and lower ethoxylates topped off in order to give an ethoxylate having about four ethylene oxide units per molecule.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of alkanols to the corresponding acids. These catalysts are generated in situ by the oxidation of a stable free radical nitroxide to an oxoammonium salt with an oxygen-containing oxidant. The stable free radical nitroxide can be obtained by the oxidation of secondary amines or hydroxylamines.

The stable free radical nitroxides which are suitable for use in the instant invention have the formula:

wherein each of R$_1$, R$_2$, R$_3$ and R$_4$ is an alkyl, aryl or heteroatom substituted alkyl groups and no hydrogen is bound to the remaining valences on the carbon atoms bound to the nitrogen. As used herein, the term "alkyl" is meant to include cycloalkyl. The alkyl (or heteroatom substituted) groups R$_1$–R$_4$ may be the same or different, and preferably contain 1 to 15 carbon atoms. Preferable, R$_1$–R$_4$ are methyl, ethyl, or propyl groups. In addition to hydrogen, the heteroatom substituents may include, halogen, oxygen, nitrogen and the like.

The remaining valences (R$_5$ and R$_6$) in formula III above may be satisfied by any atom or group except hydrogen which can bond covalently to carbon, although some groups may reduce the stabilizing power of the nitroxide and are undesirable. When R$_1$, R$_2$, R$_3$ and R$_4$ are each alkyl groups, however, at least one of R$_5$ and R$_6$ must be an aryl group. Preferably, R$_5$ and R$_6$ are substituted alkyl groups having 1 to about 15 carbon atoms wherein the substituent is selected from halogen, cyano, —COOR, wherein R is alkyl or aryl, —CONH$_2$, —OCOC$_2$H$_5$, carbonyl, or alkenyl where the double bond is not conjugated with the nitroxide moiety, or alkyl groups of 1 to about 15 carbon atoms. R$_5$ and R$_6$ together may also form a ring of five carbon atoms and up to two heteroatoms, such as O or N. Example so suitable compounds having the structure above and in which R$_5$ and R$_6$ form part of the ring are piperidinyl-1-oxyls and pyrrolidin-1-oxyls.

The

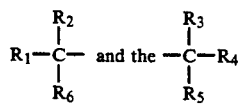

moieties in formula III above can individually be aryl, i.e.,

Examples of suitable compounds having the structure above in which the

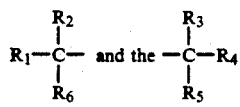

moieties are individually aryl are diphenylamine, phenyl tertiary butylamine 3-methyldipenylamines, 2-chlorophenylamine and the like. These compounds may be substituted with an substituents which do no interfere with the reaction.

In a preferred embodiment, the stable free radical nitroxide has the formula:

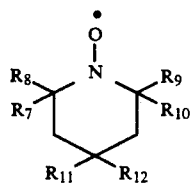

wherein each of $R_7$, $R_8$, $R_9$ and $R_{10}$ is an alkyl, aryl or heteroatom substituted alkyl group having 1 to about 15 carbon atoms and no hydrogen is bound to the remaining valences on the carbon atoms bound to the nitrogen, and each of $R_{11}$ and $R_{12}$ is alkyl, hydrogen, aryl or a substituted heteroatom. As used herein, the term "alkyl" is meant to include cycloalkyl. The alkyl (or heteroatoms substituted) groups $R_7$-$R_{10}$ may be the same or different, and preferably contain 1 to 15 carbon atoms. Preferably, $R_7$-$R_{10}$ are methyl, ethyl, or propyl groups. In addition to hydrogen, the heteroatom substituents may include, halogen, oxygen, nitrogen and the like. Preferably one of $R_{11}$ and $R_{12}$ is hydrogen, with the other one being a substituted heteroatom which does not interfere with the reaction. Suitable substituted heteroatoms include —OR,

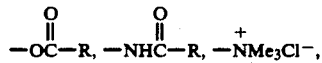

—O—SO$_3$H, —O—polymer and the like.

In a particularly preferred embodiment, the nitroxide is selected from the group consisting of 2,2,6,6-tetramethyl-piperidine-1-oxyl, 4-hydroxy-2,2,6,6-tetramethyl-piperidine-1-oxyl, 2,2,6,6-tetramethyl-piperidine-1-oxyl-4-sulfate, 4-alkoxy-2,2,6,6-tetramethyl-piperidine-1-oxyl, and mixtures thereof, with 2,2,6,6-tetramethyl-piperidine-1-oxyl, 2,2,6,6-tetramethyl-piperidine-1 -oxyl-4-sulfate, and 4-alkoxy-2,2,6,6-tetramethyl-piperidine-1-oxyl being especially preferred.

The NO$_x$-generating compound in the present process is typically selected from the group consisting of an alkali metal nitrosodisulfonate, nitric acid and mixtures thereof, with nitric acid being preferred. However, any compound which serves to generate NO$_x$ during the course of the reaction and which does not interfere with the reaction would be suitable. While not wishing to be bound by any particular theory, it is believed that nitrogen oxides (NO$_x$) are generated in the reaction and are the active species in the reaction.

The alkali metal nitrosodisulfonate suitable for use as a NO$_x$-generating compound can be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically dissolved in water prior to being added to the reaction mixture although it can be added as a solid after all of the other reactants have been added.

As used herein, the term "nitric acid" refers to nitric acid, fuming nitric acid or nitrous acid generated by contacting a nitrate or nitrite salt such as, for example, an alkali metal salt, a tetraalkylammonium salt, an alkaline earth salt or a rare earth salt, with a strong acid such as, for example, a mineral acid. The nitric acid suitable for use as a NO$_x$-generating compound in the present invention typically has a concentration in the range of from about 50 percent to about 100 percent, preferably about 70 percent. Generally, an amount of nitric acid in the range of from about 5 mole percent to about 100 mole percent, basis the moles of starting secondary alkoxyalkanol is utilized. The nitric acid is typically added to the reaction mixture after all of the other reactants have been added.

The oxidants suitable for use in the instant invention are those compounds which are capable, in the presence of a NO$_x$-generating compound, of oxidizing the stable free radical nitroxide to the oxoammonium salt. Suitable oxidants include oxygen-containing gases such as pure oxygen and oxygen in air. Whereas pure oxygen can is preferred to accomplish the desired conversion, the oxygen can also be diluted with an inert gas such as nitrogen, helium, argon, or other similar gas. While air can be used as the oxidant, the reaction rate is much slower. For purposes of increasing the reaction rate, higher O$_2$ pressures such as, for example, 1000 psig can be utilized. In a preferred embodiment, pure oxygen is used as the oxidant and it is bubbled into the reaction solution. In another embodiment, air can be bubbled initially through the reaction solution.

The amounts and concentrations of the reactants utilized in the process of the instant invention can vary within wide ranges. The amount of stable free radical nitroxide is typically in the range of from about 1 mole percent to about 50 mole percent, preferably from about 5 mole percent to about 20 mole percent, basis the number of moles starting secondary alkoxyalkanol. Generally, the amount of NO$_x$-generating compound used is in the range of from about 5 mole percent to about 100 mole percent, basis the number of moles of secondary alkoxyalkanol.

The process of the present invention is typically conducted under mild conditions, with good results being obtained using a temperature in the range of from about 0° C. to about 100° C., preferably about 20° C. to about 70° C., and most preferably, about 40° C. to about 60° C. Reaction pressures are not critical although higher pressures can result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the nitroxide.

The process of the instant invention can be carried out in a variety of ways. For example, 0.032 moles of secondary alkoxyalkanol, and 0.006 moles percent by weight of the nitroxide, may be added to the reaction vessel, followed by the addition of 0.016 moles of 70 percent nitric acid and bubbling $O_2$ through the reaction mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. Phase separation of the final product mixture takes place at 100° C. with water. The reaction product can be purified by a number of conventional means such as high temperature water washing or catalytic hydrogenation.

Depending upon process conditions and the nitroxide used, the yields of secondary alkoxyalkanoic acid obtained by this invention can be greater than about 98% of starting material being converted. The products produced by the instant process can be used in a variety of detergent applications. For example, light duty dishwashing liquids, shampoos and heavy duty laundry liquids or powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

Example 1

15.6 Grams of a secondary alkoxyalkanol (a mixture of $C_{11}$ and $C_{12}$ secondary alcohols having an average of 1 ethylene oxide unit per molecule of alcohol), 1.0 grams of 2,2,6,6-tetramethyl-piperidine-1-oxyl, and 2 grams of 70 percent nitric acid were charged to a 100 milliliter round bottomed flask. $O_2$ was bubbled through this mixture at ambient pressure. The reaction temperature was held at 60° C. over a 5-hour period. The results are presented in Table I.

Example 2

18.3 Grams of a secondary alkoxyalkanol $C_{16}$ secondary alcohol having an average of 2.6 ethylene oxide units per molecule of alcohol), 2 grams of 2,2,6,6-tetramethyl-piperidine-1-oxyl, and 2 grams of 70 percent nitric acid were charged to a 100 milliliter round bottomed flask containing 50 milliliters of dichloromethane. $O_2$ was bubbled through this mixture at ambient pressure. The reaction was held at 35° C. over a 3-hour period. The results are presented in Table I.

Example 3

Twenty-four grams of a secondary alkoxyalkanol (a mixture of $C_{11}$, $C_{12}$, $C_{13}$ and $C_{14}$ secondary alkanols having an average of three ethylene oxide units per molecule of alcohol), 1 gram of 2,2,6,6-tetramethyl-piperidine-1-oxyl, and 2 grams of 70 percent nitric acid were charged to a 100 milliliter round bottomed flask. $O_2$ was bubbled through this mixture at ambient pressure. The reaction temperature was held at 60° C. over a 5-hour period. The results are presented in Table I.

Comparative Example A

Comparative Example A was carried out in a manner similar to Example 3 except that no nitroxide was used. The results are presented in Table I.

Comparative Example B

Comparative Example B was carried out in a manner similar to Example 1 except that no nitric acid was used. The results are presented in Table I.

As can be seen in Table I, nitroxide and nitric acid are necessary for the oxidation of the secondary alkoxyalkanol to proceed.

TABLE I

Oxidation Of Secondary Alkoxyalkanols to Secondary Alkoxyalkanoic Acids

|  | % Conversion | % Sel. Acids | % Sel. Esters + Heavies | % Sel. Aldehydes |
|---|---|---|---|---|
| Example 1 | >99 | >99 | None detected | None detected |
| Example 2 | >99 | 96 | 4 | None detected |
| Example 3 | >99 | >99 | None detected | None detected |
| Comparative Example A | 2 | 0 | >99 | None detected |
| Comparative Example B | 0 | 0 | 0 | 0 |

What is claimed is:

1. A process for the preparation of a secondary alkoxyalkanoic acid of the formula $$RO(CH_2CHR'O)_nCH_2CO_2H$$

wherein R is a secondary alkyl group having from 3 to about 1000 carbon atoms, R' is hydrogen or alkyl or mixtures thereof (on the individual molecule) and n is an integer of from 1 to about 200, which comprises reacting the corresponding secondary alkoxyalkanol with a stable free radical nitroxide having the formula:

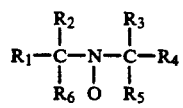

wherein
(1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$–$R_6$ are not all alkyl groups, or a substituted alkyl group having 1 to about 15 carbon atoms wherein the substituent is hydrogen, cyano, $—CONH_2$, $—OCOCH$, $OCOC_2H_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of O or N, or (2) the

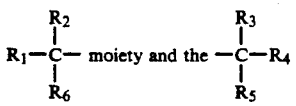

moiety individually are aryl, in the presence of a $NO_x$-generating compound and an oxidant at a temperature in the range of from about 0° C. to about 100° C. and thereafter separating out the secondary alkoxyalkanoic acid.

2. The process of claim wherein the stable free radical nitroxide has the formula:

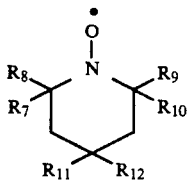

wherein each of $R_7$, $R_8$, $R_9$ and $R_{10}$ is an alkyl, aryl or heteroatom substituted alkyl group having 1 to about 15 carbon atoms and each of $R_{11}$ and $R_{12}$ is alkyl, hydrogen, aryl or a substituted heteroatom.

3. The process of claim 2 wherein the stable free radical nitroxide is selected from the group consisting of 2,2,6,6-tetramethyl-piperidine-1-oxyl, 4-hydroxy-2,2,6,6-tetramethyl-piperidine-1-oxyl, 2,2,6,6-tetramethyl-piperidine-1-oxyl-4-sulfate, 4-alkoxy-2,2,6,6-tetramethylpiperidine and mixtures thereof.

4. The process of claim 3 wherein the stable free radical nitroxide is selected from the group consisting of 2,2,6,6-tetra methyl-pi-peridine-1-oxyl,2,2,6,6-tetramethyl-piperidine-1-oxyl-4-sulfate,4-alkoxy-2,2,6,6-tetramethyl-piperidine-1-oxyl and mixtures thereof.

5. The process of claim 1 wherein said $NO_x$-generating compound is selected from the group consisting of nitric acid, an alkali metal nitrosodisulfonate and mixtures thereof.

6. The process of claim 5 wherein said $NO_x$-generating compound is nitric acid.

7. The process of claim 6 wherein said nitric acid has a concentration in the range of from about 50 percent to about 100 percent.

8. The process of claim 7 wherein said nitric acid has a concentration of about 70 percent.

9. The process of claim 5 wherein said $NO_x$-generating compound is an alkali metal nitrosodisulfonate.

10. The process of claim 5 wherein said alkali metal nitrosodisulfonate is potassium nitrosodisulfonate.

11. The process of claim 1 wherein the amount of $NO_x$-generating is in the range of from about 5 mole percent to about 100 mole percent, basis the number of moles secondary alkoxyalkanol.

12. The process of claim 11 wherein said secondary alkoxyalkanol is contacted with said stable free radical nitroxide, followed by the addition thereto of said $NO_x$-generating compound and said oxidant.

13. The process of claim 12 wherein the amount of stable free radical nitroxide is in the range of from about 1 mole percent to about 50 mole percent, basis the number of moles of secondary alkoxyalkanol.

14. The process of claim 13 wherein the amount of stable free radical nitroxide is in the range of from about 5 mole percent to about 20 mole percent, basis the number of moles of secondary alkoxyalkanol.

15. The process of claim 12 wherein the amount of $NO_x$-generating compound is in the range of from about 5 mole percent to about 100 mole percent, basis the number of moles of secondary alkoxyalkanol.

16. The process of claim 1 wherein said oxidant is an oxygen containing gas.

17. The process of claim 16 wherein said oxygen containing gas is selected from the group consisting of pure oxygen and air.

18. The process of claim 17 wherein said oxygen-containing gas is pure oxygen.

19. The process of claim 1 wherein said process is carried out at a temperature in the range of from about 20° C. to about 70° C. and at atmospheric pressure.

20. The process of claim 19 wherein said process is carried out at a temperature in the range of from about 40° C. to about 60° C. and at atmospheric pressure.

* * * * *